United States Patent [19]

Shaw et al.

[11] Patent Number: 5,001,238
[45] Date of Patent: Mar. 19, 1991

[54] PRODUCTION OF CERTAIN 2-PHENYLALKYLTHIO-AND 2-PHENYLALKYLSULFINYL IMIDAZO[4,5-C]PYRIDINES

[75] Inventors: Chia-Cheng Shaw, St-Laurent; Razzak Noureldin, Brossard; Gregory Gavin, Dollard des Ormeaux, all of Canada

[73] Assignee: American Home Products Corporation, New York, N.Y.

[21] Appl. No.: 540,050

[22] Filed: Jun. 19, 1990

[51] Int. Cl.$^5$ ............................................. C07D 471/04
[52] U.S. Cl. ..................................................... 546/118
[58] Field of Search ............................................ 546/118

[56] References Cited

U.S. PATENT DOCUMENTS 454,556  12/1989  Santilli et al. .

OTHER PUBLICATIONS

Chem. Abstracts, vol. 110-231514b (1989)—Yutilov et al., Khim. Geterotsikl. Soedin (6), pp. 799–804 (1988).
Chem. Abstracts, vol. 108-131845a (1988)—Ota et al., Japanese Kokai Tokkyo Koho JP 62,207,271 (1987).

Primary Examiner—Bernard I. Dentz
Attorney, Agent, or Firm—Walter Patton

[57] ABSTRACT

This invention relates to the process for the preparation of certain 2-phenylalkylthio- and phenylalkylsulfinyl-imidazo[4,5-c]pyridines useful for the treatment of osteoporosis.

1 Claim, No Drawings

PRODUCTION OF CERTAIN 2-PHENYLALKYLTHIO-AND 2-PHENYLALKYLSULFINYL IMIDAZO[4,5-C]PYRIDINES

BACKGROUND OF THE INVENTION

This invention relates to the process for the production of 2-substituted-imidazo[4,5-c]pyridines useful for modifying the balance between bone production and bone resorption in a host animal, including man.

Osteoporosis is a skeletal disorder which is evidenced by an increase in fracture incidence resulting from a decrease in bone density. In fact, both the bone mineral (calcium phosphate called "hydroxyapatite") and the bone matrix (major protein called "collagen") are lost. This condition may begin to occur in humans as early as age 30. In general, the process is more rapid in postmenopausal women than in men. However, after age 80 there is no sex difference in the incidence of osteoporosis. In the course of 10 to 20 years of bone loss there may be symptoms of back pain and X-ray evidence of deformation of the spine. At older ages, the brittleness of the bones becomes evident by the ease with which the proximal femur ("hip") fractures. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal. That is, new bone is continuously being formed and old bone is continuously being resorbed. However, in animals suffering from an osteoporotic condition, net bone resorption exceeds bone formation.

The present invention relates to the improved production of 2-substituted-imidazo[4,5-c]pyridines useful for the treatment of osteoporotic conditions. Said compounds are disclosed in Santilli, et al. U.S. Ser. No. 07/454,556, filed Dec. 21, 1989 and now abandoned. Santilli, et al. also disclose pharmacological data illustrating the utility of said 2-substituted-imidazo[4,5-c]pyridines in the treatment of osteoporotic conditions.

PRIOR ART

The closest prior art is Santilli, et al., U.S. Ser. No. 07/454,556, filed Dec. 21, 1989.

Santilli, et al. prepare 2-substituted-imidazo[4,5-c]pyridines according to the reaction scheme set forth below:

REACTION SCHEME 1

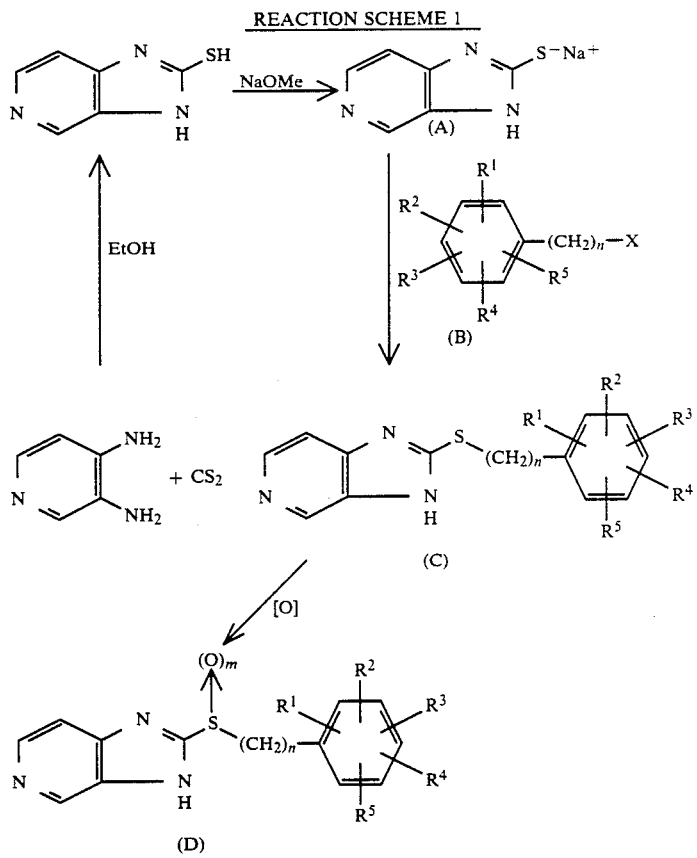

where $R^1$, $R^2$, $R^3$, $R^4$, $R^5$, m and n are as defined therein and X is Cl, Br, I or tosyl.

According to Santilli, et al. 2-substituted-imidazo[4,5-c]pyrdines are generally prepared sequentially by first forming the sodium salt of 2-mercaptoimidazo[4,5-c]pyridine (A) with sodium methoxide. Treatment of (A) in DMF with an equivalent of a suitably substituted alkylating agent (B), affords the corresponding sulfide derivative (C). Finally, oxidation of (C) with an equivalent of an oxidizing agent such as selenium dioxide/hydrogen peroxide or m-chloroperoxybenzoic acid at reduced temperature affords the desired sulfoxide.

The Santilli, et al. process is illustrated by the following Examples 1, 2 and 3.

EXAMPLE 1

2-Mercapto-1H-imidazo[4,5-c]pyridine

A mixture of 25 g (0.23 mol) of 3,4-diaminopyridine in 750 mL of ethanol containing 50 mL (63.2 g, 0.83 mol) of carbon disulfide was heated under reflux for 5 hours. The reaction mixture was allowed to cool to room temperature and the beige precipitate which had formed was collected by filtration and allowed to air dry overnight. The product amounted to 33.5 g, m.p. >320° C.

Ref. G. B. Barlin, J. Chem. Soc. (B) 285 (1966).

EXAMPLE 2

2-[[(3-Methoxyphenyl)methyl]thio]-1H-imidazo[4,5-c]pyridine

To a solution containing 3.45 g (0.15 g atom) of sodium dissolved in 800 mL of methanol was added 22.65 g (0.15 mol) of 2-mercapto-1H-imidazo[4,5-c]pyridine. The reaction mixture was stirred for ½ hour at room temperature. The solvent was removed in a rotary evaporator and to the residue was added 465 mL of DMF. 3-Methoxybenzyl chloride (23.49 g, 0.15 mol) was then added dropwise and the reaction mixture was stirred overnight at room temperature. The reaction mixture was poured into approximately 1800 mL of water and allowed to cool for several hours in an ice bath. The product was removed by filtration and amounted to 28.3 g. Recrystallization from ethyl acetate gave 18.6 g of product. An analytical sample (m.p. 133°–136° C.) was obtained by recrystallization from ethanol.

Anal. Calcd. for $C_{14}H_{13}N_3OS$: C, 61.97; H, 4.83; N, 15.49. Found: C, 61.91; H, 4.81; N, 15.48.

EXAMPLE 3

2-[[(3-Methoxyphenyl)methyl]sulfinyl]-1H-imidazo[4,5-c]pyridine

2-[[(3-Methoxyphenyl)methyl]thio]-1H-imidazo[4,5-c]pyridine (9.88 g, 0.036 mol) was dissolved in 130 mL of methanol by heating. An oxidizing solution was prepared by dissolving 4.0 g (0.036 mol) of selenium dioxide in 150 mL of methanol with heating followed by the addition of 4.07 g (0.036 mol) of 30% hydrogen peroxide and 2.5 mL of water. The oxidizing solution was cooled to room temperature and was added dropwise to the sulfide solution. The reaction mixture was stirred overnight. The precipitate which had formed was collected on a filter and rinsed with petroleum ether giving 4.68 g of product. An analytical sample (m.p. 176°–179° C.) was obtained by recrystallization from ethanol.

Anal. Calcd. for $C_{14}H_{13}N_3O_2S$: C, 58.42; H, 4.56; N, 14.62. Found: C, 58.47; H, 4.53; N, 14.62.

SUMMARY OF THE INVENTION

This invention relates to the process for the production of 2-substituted-imidazo[4,5-c]pyridine derivatives useful in inhibiting bone resorption and having the formula (I) or its tautomer having the formula (I')

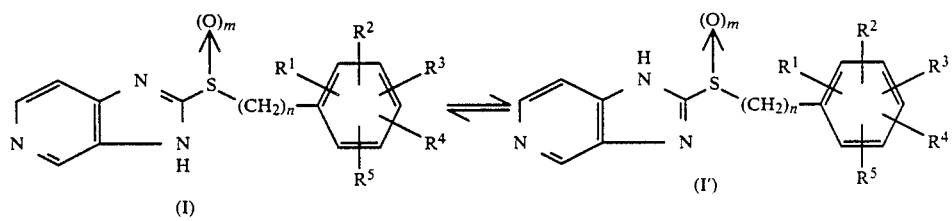

wherein $R^1$, $R^2$, $R^3$, $R^4$, and $R^5$ are independently selected from the group consisting of hydrogen, hydroxy, methoxy, fluorine, chlorine, methyl, trifluoromethyl, benzyloxy or any two adjacent groups are joined to form methylenedioxy; m is 0 to 1; n is 1 to 2, and the pharmaceutically acceptable salts thereof.

The process of the present invention is illustrated by the process for the production of 2-[[(3-methoxyphenyl)methyl]sulfinyl]-1H-imidazo[4,5-c]pyridine set forth in Reaction Scheme 2 below:

REACTION SCHEME 2

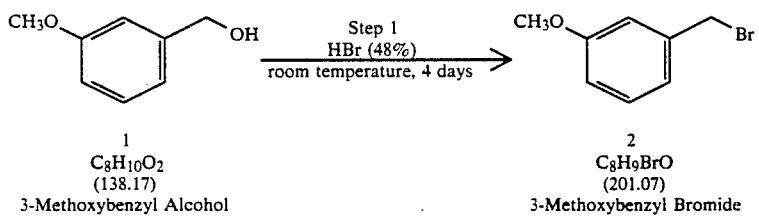

1
$C_8H_{10}O_2$
(138.17)
3-Methoxybenzyl Alcohol

2
$C_8H_9BrO$
(201.07)
3-Methoxybenzyl Bromide

-continued
REACTION SCHEME 2

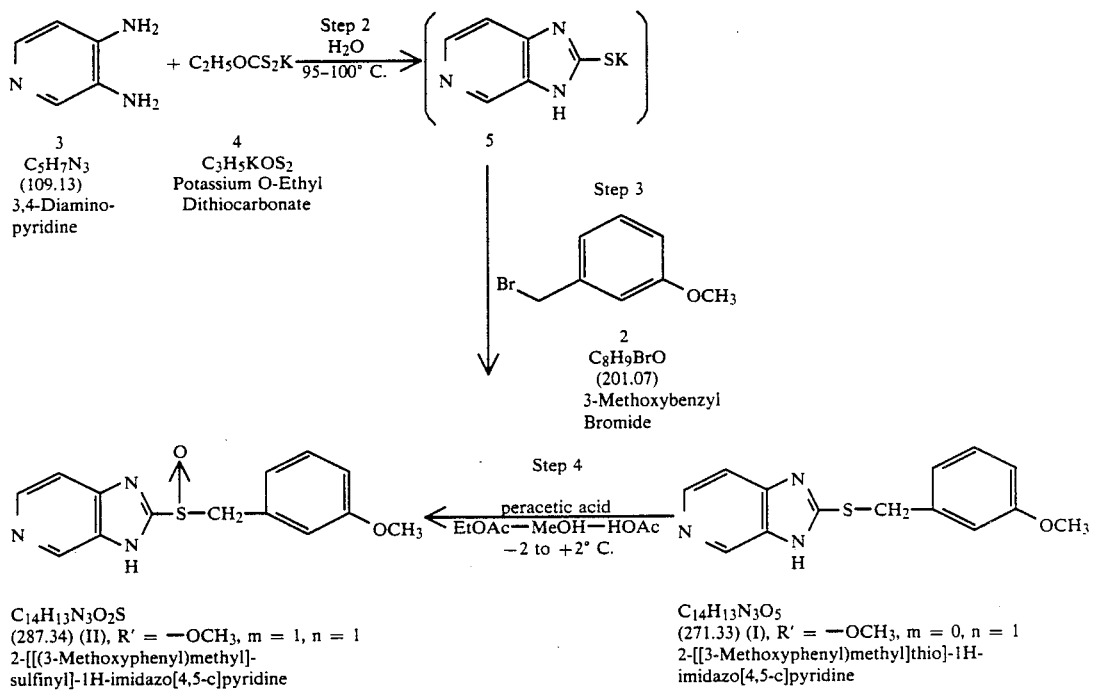

C₅H₇N₃ (109.13)
3,4-Diamino-pyridine

C₃H₅KOS₂
Potassium O-Ethyl Dithiocarbonate

C₈H₉BrO (201.07)
3-Methoxybenzyl Bromide $C_{14}H_{13}N_3O_2S$
(287.34) (II), R' = —OCH₃, m = 1, n = 1
2-[[(3-Methoxyphenyl)methyl]-sulfinyl]-1H-imidazo[4,5-c]pyridine $C_{14}H_{13}N_3OS$
(271.33) (I), R' = —OCH₃, m = 0, n = 1
2-[[3-Methoxyphenyl)methyl]thio]-1H-imidazo[4,5-c]pyridine In reference to Reaction Scheme 2, Step 1 the 3-methoxybenzyl bromide 2 is synthesized by stirring the 3-methoxybenzyl alcohol 1 with 48% hydrobromic acid at room temperature for 4 days. The crude product is obtained in 89% yield and has 84.1% strength by a quantitative GC analysis. This crude product is satisfactory for the subsequent alkylation reaction. The purification by distillation can now be avoided, since this product is a hazardous lachrymator.

According to the present invention Steps 2 and 3 to produce the compound (I), R'=—OCH₃, m=1, n=2 were carried out in a one-pot reaction instead of a two-step reaction.

Potassium O-ethyl dithiocarbonate 4 was used to replace the hazardous CS₂ for the synthesis of potassium salt of 2-mercapto-1H-imidazo[4,5-c]pyridine 5. The reaction was carried out by heating a mixture of 3,4-diaminopyridine 3 and potassium O-ethyl dithiocarbonate 4 in water at 95° to 100° C. for 8 hours. The product 5 was used in situ without isolation.

The alkylation step was carried out in aqueous methanolic media at −10° to −5° C., and 3-methoxybenzyl bromide 2 was used to replace 3-methoxybenzyl chloride to afford a shorter reaction time and to minimize the formation of di-alkylation by-product.

The isolation of the product (I), R'=—OCH₃, m=0 n=1 was simple. The product was obtained in an overall yield of 78% based on 3,4-dimethylpyridine 3 and has 97.3% strength by a quantitative HPLC analysis.

According to the present invention in Step 4 the title compound (I), R'=—OCH₃ m=1, n=1 was synthesized using peracetic acid as the oxidation agent. The starting sulfide (I), R'=—OCH₃, m=0, n=1 was converted to the corresponding sulfoxide (II), R'=—OCH₃, m=1, n=1 at −2° to +2° C. in EtOAc-MeOH-HOAc media. The isolation crude yield was 85%. This material was 97.8% pure by a qualitative HPLC analysis.

According to the present invention in Step 5 the wet crude product (I), R'=—OCH₃, m=1, n=1 was purified at 20° to 25° C. in ethanolic aqueous media containing ammonium hydroxide instead of boiling ethanol temperature conditions, thus avoiding the formation of by-product during the purification.

The crude product was dissolved in diluted ammonium hydroxide solution at 15° to 20° C. and washed with methylene chloride. The aqueous layer was then filtered to remove physical impurities. Ethanol was added to the filtrate and the pH of the solution adjusted to pH 7 to 8 using acetic acid. The product precipitated as a white solid which was then washed with water and ethyl acetate to afford 85 to 90% yield of product. This treatment removed most of the impurities.

The product was then suspended in 4 parts of ethanol to which was added half part of ammonium hydroxide (28%) to form a solution at 15° to 20° C. The solution was filtered, and the pH of the filtrate was adjusted to 7 to 8 using acetic acid. The product crystallized out as a white fine solid which was washed with water, then ethyl acetate, and dried at 75° to 80° C. under high vacuum to afford the final product.

The overall yield was 75.4% based on the starting (I), R'=—OCH₃, m=0, n=1.

As shown in REACTION SCHEME 2, the following steps are different from the prior art process of REACTION SCHEME 1.

1. The key intermediate (I), R'=—OCH₃, m=0, n=1 is synthesized in a one-pot reaction compared to the original two-step synthesis. The potassium O-ethyl dithiocarbonate is used to replace the hazardous carbon disulfide for the preparation of potassium salt of 2-mercapto-1H-imidazo[4,5-c]pyridine 5 using water as the solvent at 95° to 100° C. for 8 hours. 5 is used in situ without isolation. The alkylation is carried out in aqueous methanolic medium at −5° to −10° C. using 3-methoxybenzyl bromide instead of 3-methoxybenzyl chloride to achieve a shorter reaction time and minimize the formation of the dialkylated by-product. The isolation of (I), R'=—OCH$_3$, m=0, n=1 from the reaction mixture is simple and the overall yield from 3,4-diaminopyridine is 78% and the product strength is 97.3%.

2. The 3-methoxybenzyl bromide used in this process is synthesized by stirring a mixture of 3-methoxybenzyl alcohol and 48% hydrobromic acid at room temperature for 4 days. The product is isolated in 89% crude yield with 84% strength, and is used directly without further purification.

3. In the present process peracetic acid is used as the oxidation agent to replace selenium dioxide used in the prior art process. The compound (I), R'=—OCH$_3$, m=0, n=1 (sulfide) is converted to the corresponding sulfoxide (II), R'=—OCH$_3$, m=1, n=1 using one molar equivalent of peracetic acid in ethyl acetate-methanol-acetic acid medium. The isolation yield is 85% with 97.8% purity by a qualitative HPLC analysis.

4. The final purification step is essential for the manufacture of finished bulk drug. Because of the poor solubility of (II), R'=—OCH$_3$, m=1, n=1 in most solvents and its instability in hot organic solvent, the conventional crystallization methodology failed to purify this material. After an extensive study, we developed a unique method for the purification of the crude (II), R'=—OCH$_3$, m=1, n=1. The crude product is dissolved in diluted ammonium hydroxide solution at 15° to 20° C. and extracted with methylene chloride to remove the major impurities. The aqueous layer is separated and filtered to remove any physical impurities. Ethanol is added to the filtrate and the pH of the solution is adjusted to 7 to 8 using acetic acid. The white solid is filtered, washed with water, then ethyl acetate to afford semi-pure product. The product is re-dissolved in ethanol (4 parts) and 28% ammonium hydroxide (0.5 parts) to form a solution. The solution is filtered and the pH of the filtrate is adjusted to 7 to 8 using acetic acid. The product crystallizes as a white fine solid, which is filtered, washed with water, then ethyl acetate. After being dried at 75° to 80° C. under high vacuum, it affords the finished final product in 75.4% yield, based on the starting compound (I), R'=—OCH$_3$, m=0, n=1.

EXAMPLE 4

2-[[(3-Methoxyphenyl)methyl]sulfinyl]-1H-imidazo[4,5-c]pyridine

Step (1) Preparation of 3-Methoxybenzyl Bromide

To cooled (15° to 20° C.) hydrobromic acid (3.22 kg) (48%) is added 3-methoxybenzyl alcohol (1 kg) dropwise over a period of 1 hour. A slight exotherm results with pot temperature rising from 20° to 23° C. After the addition, the reaction mixture was stirred at 23° to 27° C. for four days. The product separated as an oil during this period. The reaction mixture was transferred to a separatory funnel, and the lower layer containing the product was separated. The aqueous phase was extracted with methylene chloride (750 mL). The methylene chloride extract was combined with the main product and washed with water (500 mL×3). The pH of the last wash was 6.5 to 7.0. The product was dried over anhydrous sodium sulfate (200 g), filtered and concentrated under reduced pressure (bath temperature 50° to 55° C.) to remove most of the solvent, then further concentrated at 40° to 45° C. under 5 mm Hg to constant weight to yield 1.30 kg (89% yield) of crude product. The presence of 5.5% of starting material in this product does not interfere with the subsequent alkylation reaction.

Step (2) and Step (3) Preparation of 2-[[3-Methoxyphenyl)methyl]thio]-1H-imidazo[4,5-c]pyridine To a solution of water (400 mL) and potassium O-ethyl dithiocarbonate (176.0 g) was added 3,4-diaminopyridine (109.1 g) in one lot.

The mixture was stirred at reflux conditions (pot temperature 95° to 100° C.) for 8 hours. Hydrogen sulfide gas generated during this period was scavenged using a 10% sodium hydroxide trap.

The resulting mixture, a dark solution, was cooled to room temperature. Methanol (44 mL) was added to prevent the precipitation of potassium salt of 2-mercapto-1H-imidazo[4,5-c]pyridine during cooling. A homogeneous solution at −10° C.±2° C. is required for the following alkylation reaction.

The mixture was further cooled to −10° C.±2° C. To this cold mixture was added dropwise a cold solution (−5° to −10° C.) of 3-methoxybenzyl bromide (236 g) in methanol (944 mL) over a period of 3 hours with pot temperature maintained at −5° to −10° C. during the addition. After the addition, the mixture was stirred at the same temperature range for 30 minutes. To this cold reaction mixture was added dropwise 500 mL of water over a period of 20 minutes with pot temperature maintained below 0° C., followed by 800 mL of methylene chloride. The mixture was stirred vigorously for 30 minutes and the lower organic layer was separated. The aqueous layer was extracted twice with methylene chloride (400 mL×2). The methylene chloride extracts were combined and washed with water (500 mL×2). The organic phase was cooled to 5° to 10° C. and 900 mL of 10% sodium hydroxide was added over a period of 20 minutes. The mixture was stirred vigorously at 10° to 15° C. for 1 hour.

The lower organic layer was separated, the basic aqueous phase was extracted once with methylene chloride (500 mL). The basic aqueous layer was separated and 600 mL of methanol was added and the resulting mixture cooled to 5° to 10° C. This cold mixture was acidified with concentrated hydrochloric acid with cooling below 15° C. to a pH of 7 to 8. At the end of addition of acid, the product oiled out and formed a cloudy mixture. The mixture was stirred at 0° to 5° C. for 5 hours. The solid product was filtered and washed with water (500 mL). The wet product was stirred vigorously with 800 mL of methylene chloride-heptane (1:1; v/v) at room temperature for 30 minutes, filtered and washed with heptane (250 mL×2).

The product was dried at 80°±2° C. under high vacuum to constant weight. It afforded 212.1 g of product as a beige-colored solid (78% yield based on 3,4-diaminopyridine).

Step (4) Preparation of 2-[[(3-Methoxyphenyl)methyl]sulfinyl]-1H-imidazo[4,5-c]pyridine To a stirred solution of ethyl acetate (2710 mL) and 2-[[(3-methoxyphenyl)methyl]thio]-1H-imidazo[4,5-c]pyridine (271.3 g) was added methanol (271 mL) and acetic acid (136 mL). The mixture was stirred at 50° to 55° C. for 30 minutes.

The solution was cooled to −5° C. and 200 mL of peracetic acid was added over a period of 1.5 hours with pot temperature maintained at −2° to 2° C. When about 160 mL of peracetic acid had been added, a mass of product precipitated.

After the addition, the mixture was stirred at the same temperature range for an additional 2 hours. The reaction mixture was further cooled to −5° C. and 250 mL of 30% sodium metabisulfite solution was added over a period of 30 minutes with pot temperature maintained below +5° C. A KI starch paper test of the reaction mixture was negative.

The reaction mixture was cooled to −5° C., and 400 mL of ammonium hydroxide was added to the reaction mixture over a period of 40 minutes with pot temperature maintained below +5° C.

After the addition, the mixture was stirred at 0° to 5° C. for 3 hours. The reaction mixture was filtered, the wet product was washed thoroughly with water (300 mL×2) then thoroughly with ethyl acetate (300 mL×2) and dried at 65° to 70° C. under high vacuum to constant weight. It afforded 244.2 g of product as an off-white solid (85% yield).

Step (5) Purification of
2-[[(3-Methoxyphenyl)methyl]sulfinyl]-1H-imidazo-[4,5-c]pyridine To a stirred suspension of 239.5 g of crude 2-[[(3-methoxyphenyl)methyl]sulfinyl]-1H-imidazo[4,5-c]pyridine in 2400 mL of water and 960 mL of methylene chloride was added dropwise 240 mL of ammonium hydroxide (28%) over a period of 20 minutes. After the addition, the mixture was vigorously stirred for an additional 30 minutes.

The layers were separated and the lower organic layer was discarded. The upper aqueous layer was washed with methylene chloride (960 mL×3).

The aqueous layer was filtered. To the aqueous layer was added 530 mL of ethanol. The solution was cooled to 15° to 20° C. with stirring. The cooled solution was acidified with acetic acid: $H_2O$ (1:1) to a pH of 8.0 to 7.0. At the end of the acidification a mass of product precipitated as a white fine solid.

The product was collected by filtration and washed with 1100 mL of water, 1.1 L of ethyl acetate and the product suspended in 840 mL of ethanol.

To the suspension was added 104 mL of ammonium hydroxide (28%) over a period of 20 minutes. The resulting hazy solution was filtered. The filtrate was acidified to pH 8.0 to 7.0 with acetic acid (75 to 84 mL required) added dropwise over a 30 minute period with cooling to 15° to 20° C.

The resulting precipitate was collected by filtration, washed with water (1000 mL×2) and ethyl acetate (1200 mL) and dried in vacuum at 75° to 80° C. to constant weight to obtain 188.5 g of pure product (74.4% yield).

We claim:

1. The process for the production of compounds of formula

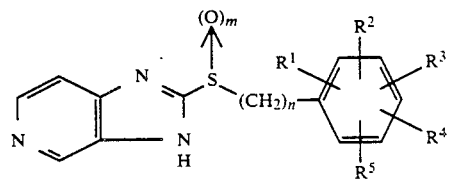

wherein $R^1$, $R^2$, $R^3$, $R^4$, and $R^5$ are independently selected from the group consisting of hydrogen, hydroxy, methoxy, fluorine, chlorine, methyl, trifluoromethyl, benzyloxy or any two adjacent groups are joined to form methylenedioxy; m is 0 to 1; n is 1 to 2, and the pharmaceutically acceptable salts thereof which comprises (a) reacting 3,4-diaminopyridine of formula 3

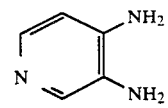

with potassium O-ethyl dithiocarbonate to produce the potassium salt of 2-mercaptoimidazo[4,5-c]pyridine of formula 5

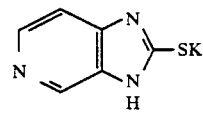

(b) reacting said potassium salt with the suitably substituted alkylating agent of formula 2

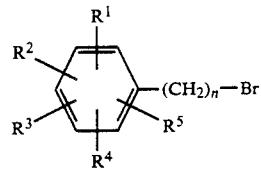

wherein $R^1$, $R^2$, $R^3$, $R^4$, and $R^5$ and n are as defined above to obtained the sulfide compound of formula (I)

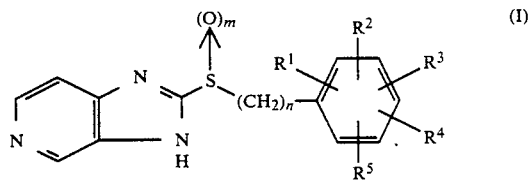

wherein $R^1$, $R^2$, $R^3$, $R^4$, $R^5$ and n are as defined above and m is 0 and oxidizing said sulfide with peracetic acid to obtain the compounds of formula (II) wherein m is 1.

* * * * *